United States Patent [19]

Friedmann et al.

[11] Patent Number: 4,987,231

[45] Date of Patent: Jan. 22, 1991

[54] OPTICAL RESOLUTION METHOD FOR 3R-(3-CARBOXYBENZYL)-6-(5-FLUORO-2-BENZOTHIAZOLYL)METHOXY-4R-CHROMANOL

[75] Inventors: Robert C. Friedmann, Old Saybrook; George J. Quallich, North Stonington, both of Conn.

[73] Assignee: Pfizer Inc., New York, N.Y.

[21] Appl. No.: 389,715

[22] Filed: Aug. 4, 1989

[51] Int. Cl.$^5$ ............................................ C07D 435/04
[52] U.S. Cl. .................................... 546/135; 546/134; 548/159
[58] Field of Search ................. 548/159; 546/134, 135

[56] References Cited

FOREIGN PATENT DOCUMENTS 313295  4/1989  European Pat. Off. .
2080304 7/1980  United Kingdom .

OTHER PUBLICATIONS

Eliel, *Stereochemistry of Carbon Compounds*, (1962), p. 52.
Chem. Abstract vol. 73, No. 44785w (1970), Paquette et al.
Gordon et al., *The Chemist's Companion*, (1973), pp. 230–231.

*Primary Examiner*—Mukund J. Shah
*Assistant Examiner*—Philip T. Datlow
*Attorney, Agent, or Firm*—Peter C. Richardson; J. Trevor Lumb; Robert K. Blackwood

[57] ABSTRACT

Preparative method for 3R-(3-carboxybenzyl)-6-(5-fluoro-2-benzothiazolyl)methoxy-4R-chromanol via its salt with quinine.

1 Claim, No Drawings

OPTICAL RESOLUTION METHOD FOR 3R-(3-CARBOXYBENZYL)-6-(5-FLUORO-2-BENZOTHIAZOLYL)METHOXY-4R-CHROMANOL

BACKGROUND OF THE INVENTION

The present invention is directed to a process for 3R-(3-carboxybenzyl)-6-(5-fluoro-2-benzothiazolyl)-methoxy-4R-chromanol, of the formula

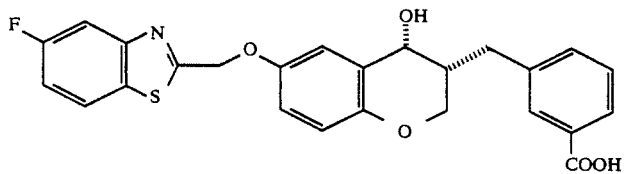

alternatively named 3R,4R-[(3-carboxyphenyl)methyl]-6-[(5-fluoro-2-benzothiazolyl)methoxy]-3,4-dihydro-2H-benzopyran-4-ol. In this process, the corresponding racemic compound, (±)-cis-(3-carboxybenzyl)-6-(5-fluoro-2-benzothiazolyl)methoxy-4-chromanol is resolved using quinine, with isolation of the pure, crystalline, less-soluble, diastereomeric quinine salt of (I) from methanol.

The compound (I) is a known inhibitor of 5-lipoxgenase enzyme and antagonist of leukotriene receptors, and so is valuable in the prevention or treatment of asthma, arthritis, psoriasis, ulcers, myocardial infarction and related disease states in mammals as detailed in published European patent application No. 313295.

The compound (I) was heretofore obtained via the methyl ester of the compound of the formula (I), which in turn had been obtained by resolution of the corresponding racemic compound via separation of diastereomeric R-0-acetylmandelate esters. This method involves the discrete chemical steps of esterification and hydrolysis. It has thus been a desirable goal to find a method for the direct resolution of the cis-acid in the form of a readily formed and decomposed diastereomeric salt, a goal which has been met by the present invention.

Quinine has been previously used in the resolution of racemic organic acids. However, its use does not assure success in any given instance, since it requires not only that the desired diastereomeric salt be crystalline, but that it be significantly less soluble than its structurally, closely related diastereomeric salt, if the desired salt is to be obtained in good yield without tedious fractional crystallization methods. See Wheland, "Advanced Organic Chemistry," 3rd Ed., John Wiley and Sons, Inc., New York, 1960, page 312; and "Left and Right Drugs," Science 84, American Association for the Advancement of Science, Washington, D.C., June, 1984, page 11.

SUMMARY OF THE INVENTION

The present invention is directed to a method for the preparation of 3S-(3-carboxybenzyl)-6-(5-fluoro-2-benxothiazolyl)methoxy-4S-chromanol, of the absolute stereochemical formula (I), as depicted above, or a pharmaceutically acceptable salt thereof, which comprises the steps of:

(a) combining racemic cis-3-(3-carboxybenzyl)-6-(5-fluoro-2-benzothiazolyl)methoxy-4-chromanol with at least a half molar quantity of quinine in methanol at a temperature in the range of about 20°-65° C., at a concentration such that the quinine salt of the compound of the formula (I) crystallizes substantially free of the quinine salt of the enantiomer of (I);

(b) conventionally recovering said quinine salt of the compound of the formula (I); and (c) conventionally acidifying said quinine salt with acid in a reaction-inert solvent to produce said compound of the formula (I).

As used above and elsewhere herein, the expression "reaction-inert solvent" refers to a solvent or solvent mixture which does not interact with starting materials, reagents, intermediates or products in a manner which adversely affects the yield of the desired product.

The present invention is also directed to that process further comprising recovering as by-product crude quinine salt of enantiomeric 3S-(3-carboxybenzyl)-6-(5-fluoro-2-benzothiazolyl)methoxy-4S-chromanol from the mother liquors of said quinine salt of the compound of the formula (I), acid hydrolysis of said 3S,4S-salt to form the corresponding 3S,4S-free acid, oxidation of said free acid with Jones Reagent to form the corresponding 3S,4-chromanone, and racemization of said 3S,4-chromanone to form racemic 3-(3-carboxybenzyl)-6-(5-fluoro-2-benzothiazolyl)methoxy-4-chromanone; and to the quinine salt of 3R-(3-carboxybenzyl)-6-(5-fluoro-2-benzothiazolyl)methoxy-4R-chromanol, per se.

DETAILED DESCRIPTION OF THE INVENTION

The present invention is readily carried out. Thus, racemic cis-3-(3-carboxybenzyl)-6-(5-fluoro-2-benxothiazolyl)methoxy-4-chromanol is simply combined with at least 0.5 molar equivalents of quinine (usually about 1 molar equivalent to facilitate recovery of the diastereomeric salt, i.e., the undesired enantiomer, for recycling. The amount of methanol is set at a level which leads to high recovery of the desired salt, with minimal or no concurrent recovery of the undesired salt. For example, when the desired product is recovered at ambient temperature (about 20°-27° C.), the final volume will be about 20-30 ml/g of racemate introduced. The quality of the salt is improved by using sufficient methanol to form a clarifiable solution in refluxing methanol (e.g., about 30 ml of methanol/g of racemate), with distillative reduction in the volume of the filtrate from the clarification. It is preferred to reduce volumes and temperatures slowly, and to isolate the product after a period of digestion, e.g., 2-20 hours at ambient temperature.

The intermediate quinine salt is conventionally hydrolyzed to form the desired enantiomeric free acid of the above formula (I) by treatment with a strong acid (generally of $pK_a$ less than 3; at least one molar equivalent) in a reaction-inert solvent. Particularly convenient are mineral acids (such as HCl or $H_2SO_4$) or an organic sulfonic acid (such as $CH_3SO_3H$ or $C_6H_6SO_3H$) in water in the presence of a water-immiscible organic solvent such as ethyl acetate which will extract the desired free acid as it is formed. Temperature is not critical, but is conveniently ambient so as to avoid the cost of heating or cooling. The product is conventionally recovered from the organic solvent, e.g., by stripping and/or by the addition of a non-solvent.

For purposes of recycling, the crude 3R,4R-enantiomer, preferably in the form of its diastereomeric quinine salt, is conventionally recovered from mother liquors by stripping and/or the addition of a nonsolvent. This salt is hydrolyzed as above, oxidized (e.g., with Jones Reagent according to methods detailed in EP 313295 (cited above) and the resulting ketone racemized by the action of a strong base (usually an excess of that necessary to convert the carboxylic acid to its salt, e.g., about 110 mol% of sodium methoxide in methanol) at a temperature in the range of 0°–50° C., conveniently ambient temperature. For purposes of recycling, the racemic ketone is reduced to the corresponding C.4 alcohol (the starting material of the present method) by reduction, again according to methods in cited EP 313295.

The present invention is illustrated by the following example, but is not limited to the details thereof.

EXAMPLE 3R-(3-Carboxybenzyl)-6-(5-fluoro-2-benzo-thiazolyl)-methoxy-4R-chromanol (I)

Racemic cis-3-(3-carboxybenzyl)-6-(5-fluoro-2-benzo-thiazolyl)methoxy-4-chromanol (15.0 g, 32.2 mmole) was added slowly to boiling methanol (400 ml) on a steam bath until solution was obtained. Quinine (12.3 g, 32.4 mmole) was dissolved in methanol (50 ml) and the two solutions combined and allowed to cool with stirring for 3 days. The quinine salt of title product as a white solid was collected by vacuum filtration, washed with methanol and air dried (11.78 g; m.p. 201°–203.5° C.). This quinine salt (11.72 g) was added in portions to boiling methanol (1050 ml). When solution was obtained, the hot solution was filtered through fluted filter paper to remove a haze, and the volume then reduced to 320 ml by atmospheric distillation of the solvent. After concentration of the solution, crystallization commenced immediately and was allowed to proceed overnight at ambient temperature. The white solid product was collected by vacuum filtration, and air dried to give 9.4 g of purified quinine salt of title product (m.p. 204°–206° C.). $[\text{alpha}]_D^{25} = -32.8°$ (methanol, c=0.56). To a rapidly stirring biphasic mixture of hydrochloric acid (1N, 75 ml) and ethyl acetate (200 ml) was added the quinine salt (9.34 g). The phases were separated and the aqueous phase extracted again with ethyl acetate (100 ml). The combined organic phases were dried with sodium sulfate (10 g), filtered, and concentrated to 75 ml. Present title product (4.94 g), which crystallized as a white solid on standing, was collected by filtration and air dried; m.p. 186°–188° C.; $[\text{alpha}]_D^{25} = +83.3°$ (tetrahydrofuran, c=0.47).

The filtrate from isolation of the above quinine salt is stripped to yield the impure diasteromeric quinine salt, i.e., the quinine salt of the enantiomer of title product. The latter is hydrolyzed in like manner to yield the 3S,4S-enantiomer of present title product, primarily useful for purposes of recycling to present starting material.

We claim:

1. The quinine salt of 3R-(3-carboxybenzyl)-6-(5-fluoro-2-benzothiazolyl)methoxy-4R-chromanol.

* * * * *